(12) United States Patent
Genet et al.

(10) Patent No.: US 6,468,316 B1
(45) Date of Patent: Oct. 22, 2002

(54) USE OF CATIONIC DIBENZENIC NITRO COMPOUNDS FOR DYEING KERATIN FIBERS, DYE COMPOSITIONS AND DYEING PROCESSES

(75) Inventors: Alain Genet, Aulnay sous Bois; Alain Lagrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/479,080

(22) Filed: Jan. 7, 2000

(30) Foreign Application Priority Data

Jan. 8, 1999 (FR) .............................. 99 00149

(51) Int. Cl.$^7$ ................................ A61K 7/13
(52) U.S. Cl. ........................ 8/405; 8/405; 8/406; 8/411; 8/415
(58) Field of Search ........................... 8/405, 415, 406, 8/411

(56) References Cited

U.S. PATENT DOCUMENTS

| | | | |
|---|---|---|---|
| 3,817,698 A | 6/1974 | Kalopissis et al. | 8/10.1 |
| 4,018,556 A | 4/1977 | Kalopissis et al. | 8/10.1 |
| 4,888,025 A | 12/1989 | Bugaut et al. | 8/405 |
| 5,135,543 A | 8/1992 | Chan et al. | 8/405 |
| 5,139,532 A | 8/1992 | Chan t al. | 8/405 |
| 5,256,823 A | 10/1993 | Chan et al. | 564/284 |
| 5,735,910 A | 4/1998 | Lagrange et al. | 8/415 |
| 5,874,618 A | 2/1999 | Lagrange et al. | 564/305 |

FOREIGN PATENT DOCUMENTS

| | | |
|---|---|---|
| BE | 616 439 | 10/1962 |
| DE | 198 02 940 | 8/1999 |
| EP | 0 673 926 | 9/1995 |
| FR | 1 221 122 | 5/1960 |
| FR | 1 565 247 | 4/1969 |
| FR | 2 520 358 | 7/1983 |
| GB | 909 700 | 10/1962 |
| GB | 1 164 824 | 9/1969 |
| GB | 1 199 641 | 7/1970 |
| LU | 54 049 | 3/1969 |
| WO | WO-9801418 | * 1/1998 |
| WO | WO 99/03836 | 1/1999 |

OTHER PUBLICATIONS

Chemical Abstracts, vol. 72, No. 2, Jan. 12, 1970, Abstract No. 4329y (JP 06 910910).

English language Derwent Abstract of DE 198 02 940, Aug. 5, 1999.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner L.L.P.

(57) ABSTRACT

The subject of the invention is dyeing compositions containing dibenzenic nitro compounds comprising at least one cationic group Z, Z being chosen from quaternized aliphatic chains, aliphatic chains comprising at least one quaternized saturated ring and aliphatic chains comprising at least one quaternized unsaturated ring, their use as direct dyes in dyeing applications for keratin substances, in particular human keratin fibers and especially the hair, and to the direct dyeing process employing these compositions.

22 Claims, No Drawings

USE OF CATIONIC DIBENZENIC NITRO COMPOUNDS FOR DYEING KERATIN FIBERS, DYE COMPOSITIONS AND DYEING PROCESSES

The present invention relates to dyeing compositions containing dibenzenic nitro compounds comprising at least one cationic group Z chosen from quaternized aliphatic chains, aliphatic chains comprising at least one quaternized saturated ring and aliphatic chains comprising at least one quaternized unsaturated ring, to the use of such compositions as direct dyes in dyeing applications for keratin substances, in particular human keratin fibers and especially the hair, and to the direct dyeing processes employing such compositions.

In the field of hair dyeing, direct dyes are sought, i.e., dyes which, without supplying any oxidizing agent other than ambient air, are capable by themselves of temporarily modifying the natural shade of the hair. In this application, the dyes must satisfy a certain number of criteria, and in particular they must generate reproducible dyeing results with rich and varied shades, thus making it possible to obtain a wide range of colors capable of satisfying the formulator, it also being necessary for these dyeing results to be intense and fast with respect to washing, rubbing, light and perspiration.

The inventors have now just discovered, entirely surprisingly and unexpectedly, that dibenzenic nitro compounds of formula (I) defined below, comprising at least one cationic group Z chosen from quaternized aliphatic chains, aliphatic chains comprising at least one quaternized saturated ring and aliphatic chains comprising at least one quaternized unsaturated ring, are suitable for use as direct dyes for direct dyeing, and also that they make it possible to obtain dye compositions which lead to intense and varied colorations which have excellent properties of fastness with respect to the various treatments to which the keratin fibers may be subjected. Finally, these compounds have better solubility in the media conventionally used for dyeing keratin fibers and are found to be easy to synthesize.

These discoveries form the basis of the present invention.

A subject of the invention is thus the use, as direct dyes in, or for the manufacture of, dye compositions for keratin substances, and in particular for human keratin fibers such as the hair, of dibenzenic nitro compounds of formula (I) below, and the acid-addition salts thereof:

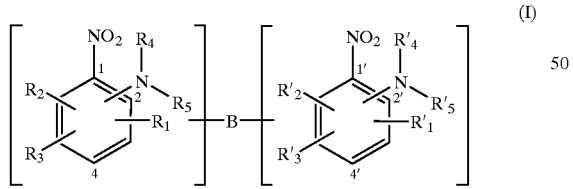

(I)

in which:
  B is a linker arm which represents a linear or branched alkyl chain preferably comprising from 1 to 14 carbon atoms, which can be interrupted with one or more groups Z and/or with one or more hetero atoms such as oxygen, sulphur or nitrogen atoms, and optionally substituted with one or more hydroxyl or $C_1$–$C_6$ alkoxy radicals, and which can bear one or more ketone functions;
  $R_1$, $R_2$, $R_3$, $R'_1$, $R'_2$ and $R'_3$, which may be identical or different, represent one of the two valencies of a linker arm B; a hydrogen atom; a halogen atom; a group Z; a ($C_1$–$C_6$)alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino-($C_1$–$C_6$)-alkylcarbonyl radical; an N,N-di($C_1$–$C_6$)alkylamino($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$)alkyl radical; an N—($C_1$–$C_6$)alkylamino-($C_1$–$C_6$)alkylcarbonyl($C_1$–$C_6$)alkyl radical; an N,N-di($C_1$–$C_6$)alkylamino($C_1$–$C_6$)-alkylcarbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N—Z-aminosulphonyl radical; an N—($C_1$–$C_6$)alkylaminosulphonyl radical; an N,N-di($C_1$–$C_6$)alkylaminosulphonyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ trifluoroalkyl radical; a cyano radical; an unsubstituted or substituted amino radical, in which the substituents on the amine, which may be identical or different, have the same meanings as the variables $R_4$, $R_5$, $R'_4$ and $R'_5$ described below; an amino($C_1$–$C_6$)alkyl radical in which the alkyl is unsubstituted or substituted with one or more hydroxyl radicals and in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$)alkylcarbamyl or N,N-di($C_1$–$C_6$)alkylcarbamyl, $C_1$–$C_6$ alkylsulphonyl, formyl, trifluoro ($C_1$–$C_6$)alkylcarbonyl, ($C_1$–$C_6$)alkylcarboxyl and thiocarbamyl radicals, or with a group Z; or a group $OR_6$ or —$SR_6$; $R_6$ denotes one of the two valencies of a linker arm B; a hydrogen atom; a $C_1$–$C_6$ alkyl radical; a $C_1$–$C_6$ monohydroxyalkyl radical; a $C_2$–$C_6$ polyhydroxyalkyl radical; a group Z; a ($C_1$–$C_6$)alkoxy($C_1$–$C_6$) alkyl radical; an aryl radical; a benzyl radical; a carboxy($C_1$–$C_6$)alkyl radical; a ($C_1$–$C_6$)alkylcarboxy ($C_1$–$C_6$)alkyl radical; a cyano($C_1$–$C_6$)alkyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$) alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro-($C_1$–$C_6$)alkylcarbonyl, ($C_1$–$C_6$)alkylcarboxyl, carbamyl, N—($C_1$–$C_6$) alkylcarbamyl, N,N-di-($C_1$–$C_6$)alkylcarbamyl, thiocarbamyl and $C_1$–$C_6$ alkylsulphonyl radicals, or with a group Z;

$R_4$, $R_5$, $R'_4$ and $R'_5$, which may be identical or different, represent one of the two valencies of a linker arm B; a hydrogen atom; a group Z; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a thiocarbamyl($C_1$–$C_6$)alkyl radical; a $C_1$–$C_6$ trifluoroalkyl radical; a $C_1$–$C_6$ sulphoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the alkyl is unsubstituted or substituted with one or more hydroxyl radicals and in which the amine is substituted with one or two identical or different radicals chosen from alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$)alkyl-carbamyl or N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z;

Z is chosen from the unsaturated cationic groups of formulae (II) and (III) below, and the saturated cationic groups of formula (IV) below:

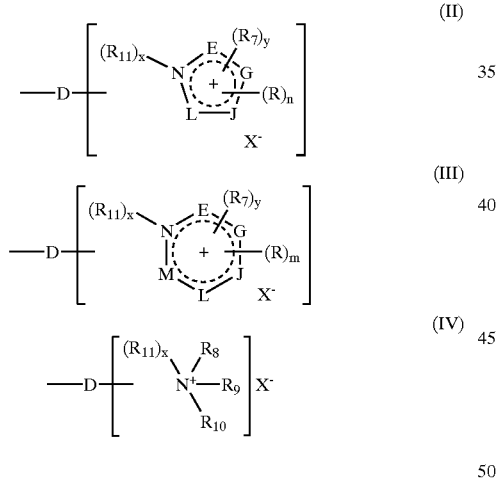

in which:

D is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1$–$C_6$ alkoxy radicals, and which can bear one or more ketone functions;

the ring members E, G, J, L and M, which may be identical or different, represent a carbon, oxygen, sulphur or nitrogen atom;

n is an integer ranging from 0 to 4;

m is an integer ranging from 0 to 5;

the radicals R, which may be identical or different, represent one of the two valencies of a linker arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a cyano($C_1$–$C_6$)alkyl radical; a $C_1$–$C_6$ alkoxy radical; a tri($C_1$–$C_6$)alkylsilane($C_1$–$C_6$)alkyl radical; an amido radical; an aldehydo radical; a carboxyl radical; a ($C_1$–$C_6$)alkylcarbonyl radical; a thio radical; a $C_1$–$C_6$ thioalkyl radical; a $C_1$–$C_6$ alkylthio radical; an amino radical; an amino radical protected with a ($C_1$–$C_6$)alkylcarbonyl, carbamyl or $C_1$–$C_6$ alkylsulphonyl radical; or a group NHR" or NR"R"' in which R" and R"', which may be identical or different, represent a $C_1$–$C_6$ alkyl radical, a $C_1$–$C_6$ monohydroxyalkyl radical or a $C_2$–$C_6$ polyhydroxyalkyl radical;

$R_7$ represents one of the two valencies of a linker arm B; a $C_1$–$C_6$ alkyl radical; a $C_1$–$C_6$ monohydroxyalkyl radical; a $C_2$–$C_6$ polyhydroxyalkyl radical; a cyano($C_1$–$C_6$)alkyl radical; a tri($C_1$–$C_6$)alkylsilane($C_1$–$C_6$)alkyl radical; a ($C_1$–$C_6$)alkoxy($C_1$–$C_6$)alkyl radical; a carbamyl-($C_1$–$C_6$)alkyl radical; a ($C_1$–$C_6$)alkylcarboxy($C_1$–$C_6$)-alkyl radical; a benzyl radical; or a second group Z which is identical to or different from the first group Z;

$R_8$, $R_9$ and $R_{10}$, which may be identical or different, represent one of the two valencies of a linker arm B; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a cyano($C_1$–$C_6$)alkyl radical; an aryl radical; a benzyl radical; a $C_1$–$C_6$ amidoalkyl radical; a tri($C_1$–$C_6$)alkylsilane($C_1$–$C_6$)alkyl radical; or a $C_1$–$C_6$ aminoalkyl radical in which the amine is protected with a ($C_1$–$C_6$)alkylcarbonyl, carbamyl or $C_1$–$C_6$ alkylsulphonyl radical; two of the radicals $R_8$, $R_9$ and $R_{10}$ can together also form, with the nitrogen atom to which they are attached, a saturated 5- or 6-membered carbon-based ring which can contain one or more hetero atoms such as, for example, a pyrrolidine ring, a piperidine ring, a piperazine ring or a morpholine ring, it being possible for the ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical; one of the radicals $R_8$, $R_9$ and $R_{10}$ can also represent a second group Z which is identical to or different from the first group Z;

$R_{11}$ represents one of the two valencies of a linker arm B; a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or $C_1$–$C_6$ alkylsulphonyl radical; a carboxy ($C_1$–$C_6$)alkyl radical; a cyano($C_1$–$C_6$)alkyl radical; a carbamyl($C_1$–$C_6$)alkyl radical; a $C_1$–$C_6$ trifluoroalkyl radical; a tri($C_1$–$C_6$)alkylsilane-($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; or an N—($C_1$–$C_6$)alkylsulphonamido($C_1$–$C_6$)alkyl radical;

x and y are integers equal to 0 or 1; with the following conditions:

in the unsaturated cationic groups of formula (II):
   when x=0, the linker arm D is attached to the nitrogen atom,
   when x=1, the linker arm D is attached to one of the ring members E, G, J or L,
   y can take the value 1 only:
      1) when the ring members E, G, J and L simultaneously represent a carbon atom and when the radical $R_7$ is borne by the nitrogen atom of the unsaturated ring; or alternatively
      2) when at least one of the ring members E, G, J and L represents a nitrogen atom to which the radical $R_7$ is attached;

in the unsaturated cationic groups of formula (III):
   when x=0, the linker arm D is attached to the nitrogen atom,
   when x=1, the linker arm D is attached to one of the ring members E, G, J, L or M,
   y can take the value 1 only when at least one of the ring members E, G, J, L and M represents a divalent atom and when the radical $R_7$ is borne by the nitrogen atom of the unsaturated ring;

in the cationic groups of formula (IV):
   when x=0, then the linker arm D is attached to the nitrogen atom bearing the radicals $R_8$ to $R_{10}$,
   when x=1, then two of the radicals $R_8$ to $R_{10}$ form, together with the nitrogen atom to which they are attached, a saturated 5- or 6-membered ring as defined above; and the linker arm D is borne by a carbon atom of the saturated ring;

$X^-$ represents a monovalent or divalent anion and is preferably chosen from a halogen atom such as chlorine, bromine, fluorine or iodine, a hydroxide, a hydrogenosulphate or a $C_1$–$C_6$ alkyl sulphate such as, for example, a methyl sulphate or an ethyl sulphate;

it being understood that the number of cationic groups Z is at least equal to 1.

In formulae (I), (II), (III) and (IV) above the alkyl and alkoxy radicals can be linear or branched.

The compounds of formula (I) can optionally be salified with strong inorganic acids such as HCl, HBr or $H_2SO_4$, or with organic acids such as acetic acid, tartaric acid, lactic acid, citric acid or succinic acid.

Among the rings of the unsaturated groups Z of formula (II) above, mention may be made in particular, for example, of pyrrole, imidazole, pyrazole, oxazole, thiazole and triazole rings.

Among the rings of the unsaturated groups Z of formula (III) above, mention may be made in particular, for example, of pyridine, pyrimidine, pyrazine, oxazine and triazine rings.

Among the compounds of formula (I) above which may be mentioned in particular are the compounds of formulae $(I)_1$ to $(I)_{23}$ below:

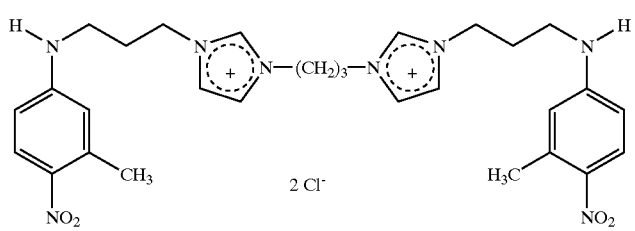

$(I)_1$

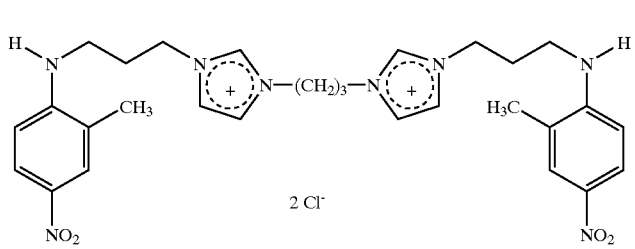

$(I)_2$

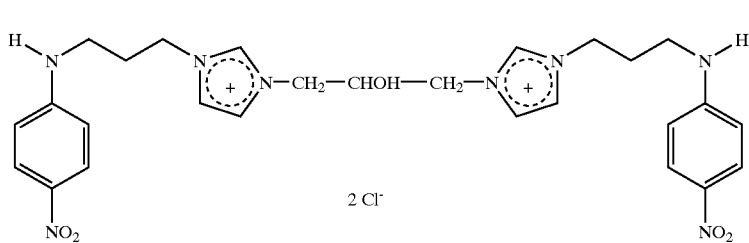

$(I)_3$ (I)4
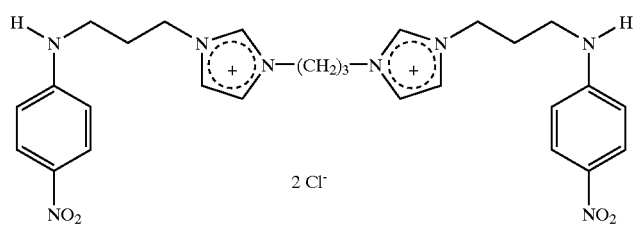
(I)5
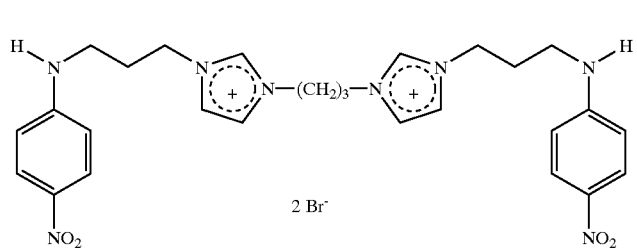
(I)6
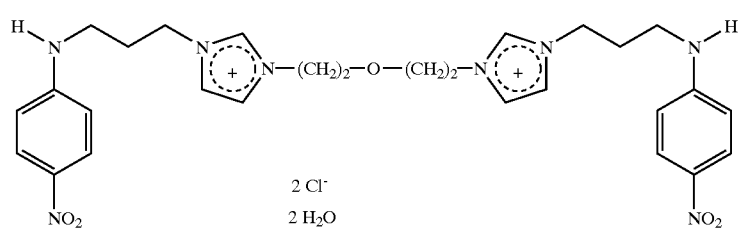
(I)7
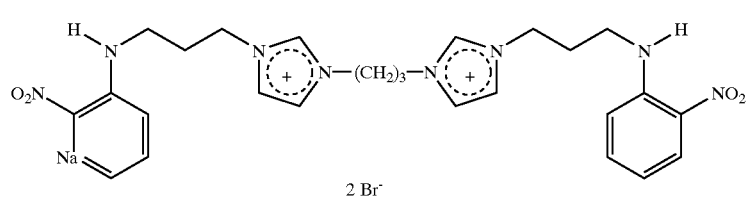
(I)8
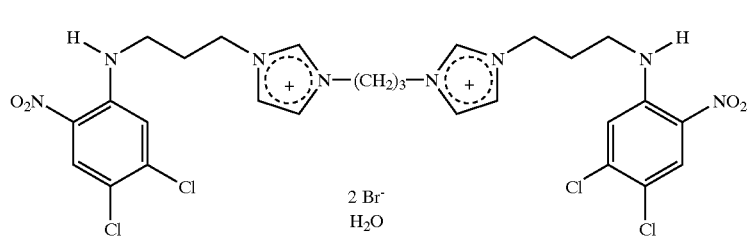
(I)9
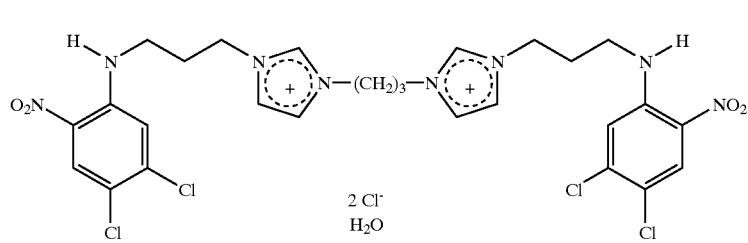

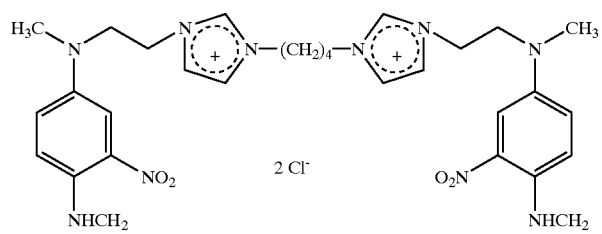
(I)₁₀
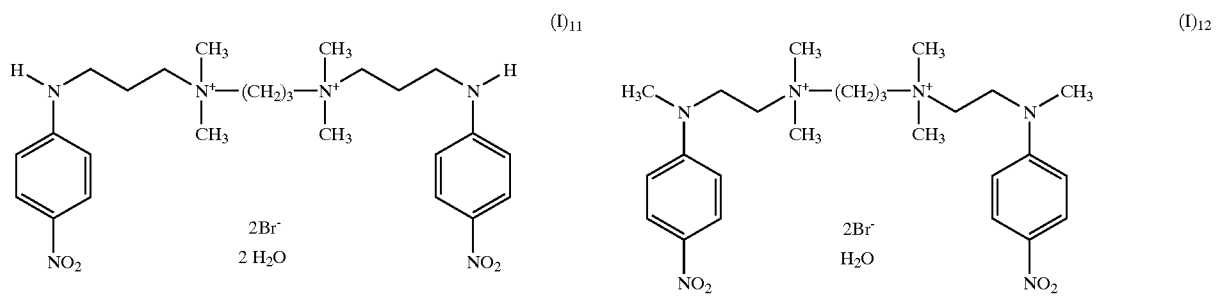
(I)₁₁            (I)₁₂
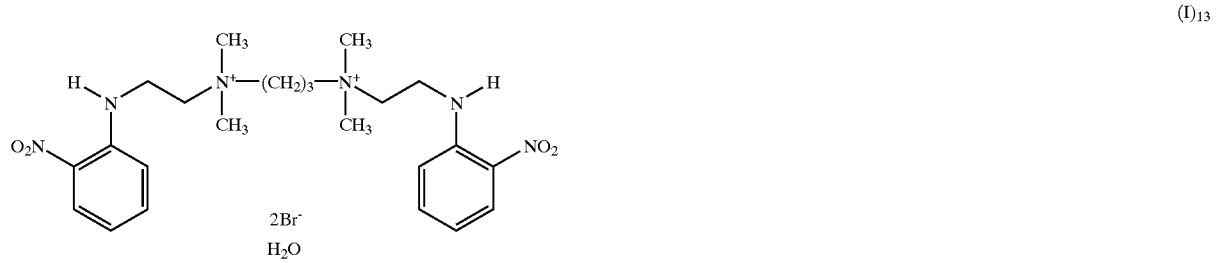
(I)₁₃
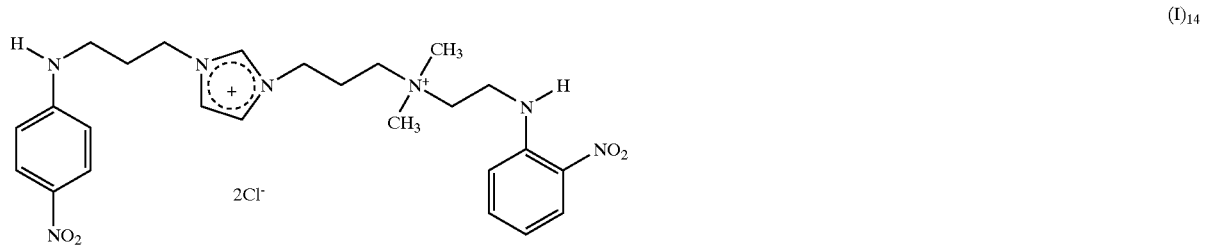
(I)₁₄
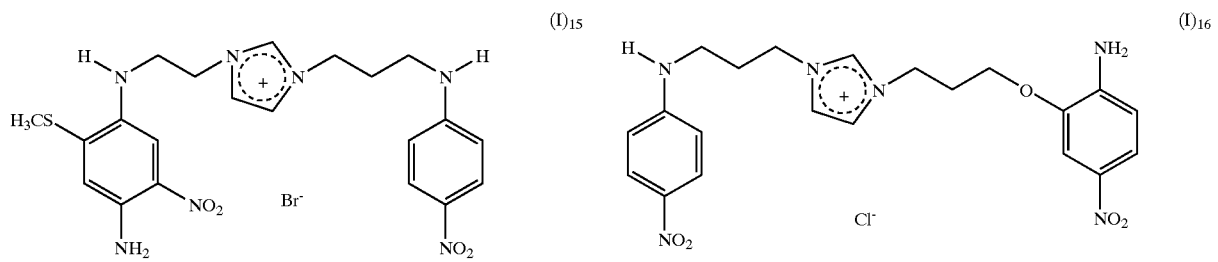
(I)₁₅            (I)₁₆
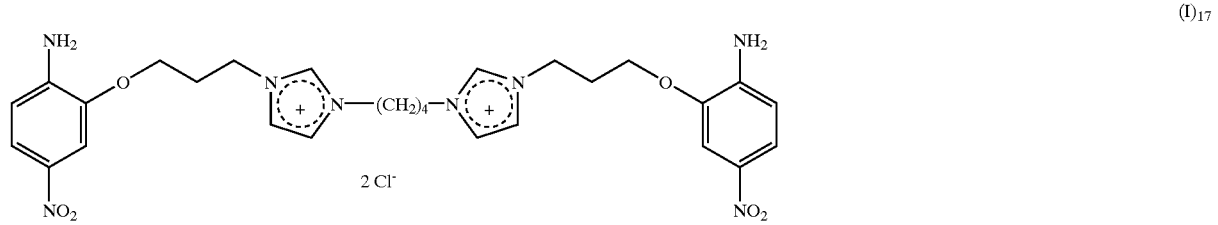
(I)₁₇

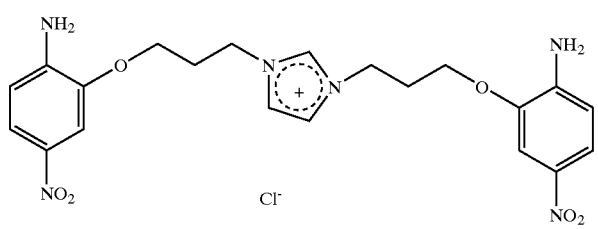

(I)₁₈

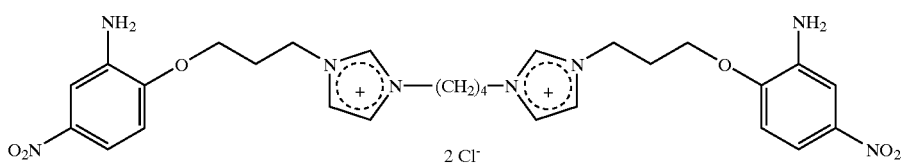

(I)₁₉

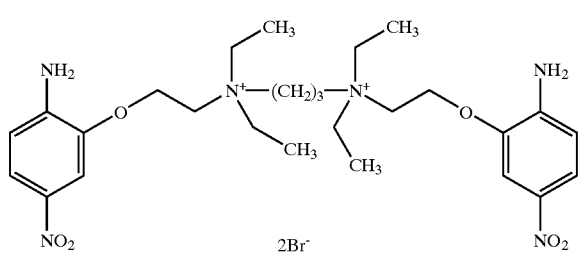

(I)₂₀

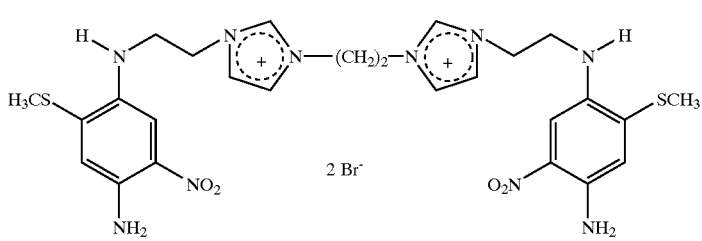

(I)₂₁

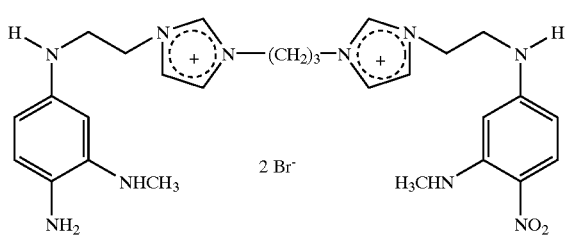

(I)₂₂

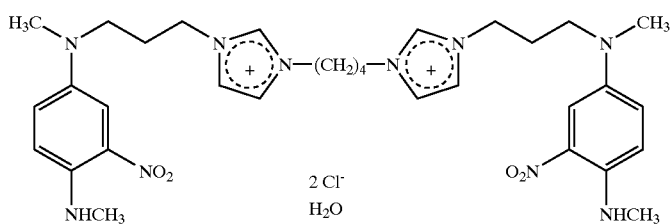

(I)₂₃

The compounds of formula (I) in accordance with the invention can be obtained easily, according to processes that are generally well known in the prior art, and in particular, for example, by:

- condensation of two molecules of a nitrobenzene bearing a haloalkyl radical with one molecule of a compound bearing two tertiary amine radicals separated by a linker arm B as defined in formula (I) described above, or alternatively by
- condensation of two molecules of a nitrobenzene bearing a tertiary amine radical with one molecule of a compound bearing two halogen radicals separated by a linker arm B as defined in formula (I) described above, or alternatively
- (a) condensation of one molecule of a nitrobenzene bearing a tertiary amine radical with one molecule of a compound bearing two halogen radicals separated by a linker arm B as defined in formula (I) described above, and (b) condensation of a second molecule of a nitro-benzene which is different from the first and which itself also bears a tertiary amine radical, or alternatively
(a) condensation of one molecule of a nitrobenzene bearing a haloalkyl radical with one molecule of a compound bearing two tertiary amine radicals separated by a linker arm B as defined in formula (I) described above, and (b) condensation of a second molecule of a nitrobenzene which is different from the first and which itself also bears a haloalkyl radical, or alternatively
condensation of one molecule of a nitrobenzene bearing a tertiary amine radical with one molecule of a nitrobenzene bearing a haloalkyl radical.

The quaternization step is generally, for convenience, the final step of the synthesis, but can be involved earlier in the sequence of reactions leading to the preparation of the compounds of formula (I).

A subject of the invention is also a composition for dyeing keratin substances, characterized in that it comprises, in a medium which is suitable for dyeing, an effective amount of at least one compound of formula (I) in accordance with the invention.

A subject of the invention is also a compound for the direct dyeing of human keratin fibers such as the hair, characterized in that it comprises, in a medium which is suitable for dyeing, an effective amount of at least one compound of formula (I) in accordance with the invention.

The cationic dibenzenic nitro compound(s) of formula (I) in accordance with the invention and/or the addition salt(s) thereof with an acid preferably represent from 0.005 to 12% by weight approximately relative to the total weight of the dye composition, and even more preferably from 0.05 to 6% by weight approximately relative to this weight.

The compounds of formula (I) in accordance with the invention can also serve in the well-known processes of oxidation dyeing, using oxidation dyes (oxidation dye precursors and optionally couplers), to modify the shade of or enrich with glints the dyeing effects obtained with oxidation dyes.

The dye composition according to the invention can also contain, to broaden the range of shades and obtain varied tints, besides the cationic dibenzenic nitro compounds of formula (I) according to the invention, other direct dyes conventionally used, and in particular nitrobenzene dyes, such as nitrophenylene diamines, nitrodiphenylamines, nitro-anilines, nitrophenyl ethers or nitrophenols, and nitropyridines, anthraquinone dyes, mono- or diazo dyes, triarylmethane dyes, azine dyes, acridine dyes and xanthine dyes, or alternatively metalliferous dyes.

The proportion of all these other additional direct dyes can range from 0.5 to 10% by weight approximately relative to the total weight of the dye composition.

The medium which is suitable for dyeing (or support) generally comprises water or a mixture of water and at least one organic solvent to dissolve the compounds which would not be sufficiently soluble in water. Examples of organic solvents which may be mentioned, for example, are $C_1$–$C_4$ lower alkanols, such as ethanol and isopropanol; glycerol; glycols and glycol ethers such as 2-butoxyethanol, propylene glycol and propylene glycol monomethyl ether; as well as aromatic alcohols such as benzyl alcohol or phenoxyethanol; and similar products and mixtures thereof.

The solvents can be present in proportions preferably ranging from 1 to 40% by weight approximately relative to the total weight of the dye composition, and even more preferably from 5 to 30% by weight approximately.

Fatty amides such as mono- and diethanolamides of acids derived from coconut, of lauric acid or of oleic acid can also be added to the composition according to the invention, at concentrations ranging from about 0.05 to 10% by weight.

Surfactants that are well known in the state of the art and of anionic, cationic, nonionic, amphoteric or zwitterionic type, or mixtures thereof, can also be added to the composition according to the invention, preferably in a proportion ranging from 0.1 to 50% by weight and advantageously from about 1 to 20% by weight relative to the total weight of the composition.

Thickeners can also be used in a proportion ranging from about 0.2 to 5%.

The dye composition can also contain various common adjuvants such as antioxidants, fragrances, sequestering agents, dispersing agents, hair conditioners, preserving agents and opacifiers, as well as any other adjuvant usually used for dyeing keratin substances.

Needless to say, a person skilled in the art will take care to select the optional additional compound(s) mentioned above, such that the advantageous properties intrinsically associated with the dye composition according to the invention are not, or are not substantially, adversely affected by the addition(s) envisaged.

The pH of the dye composition in accordance with the invention is generally from 3 to 12 approximately, and preferably from 5 to 11 approximately. It can be adjusted to the desired value using acidifying or basifying agents commonly used to dye keratin fibers.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

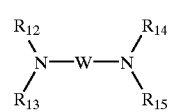

(V)

in which W is a propylene residue optionally substituted with a hydroxyl group or a $C_1$–$C_6$ alkyl radical; and $R_{12}$, $R_{13}$, $R_{14}$ and $R_{15}$, which may be identical or different, represent a hydrogen atom, a $C_1$–$C_6$ alkyl radical or a $C_1$–$C_6$ hydroxyalkyl radical.

The dye composition according to the invention can be in various forms, such as in the form of liquids, creams, gels or any other form which is suitable for dyeing keratin substances, and especially human hair. In particular, it can be packaged under pressure in an aerosol can in the presence of a propellant and form a mousse.

Another subject of the invention relates to a process for dyeing keratin fibers, and in particular human keratin fibers such as the hair, by direct dyeing, which comprises the step of leaving a composition containing at least one cationic dibenzenic nitro compound of formula (I) to act on wet or dry keratin fibers.

The composition according to the invention can be used as a leave-in composition, i.e. after applying the composition to the fibers, they are dried without intermediate rinsing.

In the other application methods, after applying the composition to the fibers for an exposure time ranging from 3 to 60 minutes approximately, preferably from 5 to 45 minutes approximately, the fibers are rinsed, optionally washed, and then rinsed again and dried.

Concrete and non-limiting examples illustrating the invention will now be given.

PREPARATION EXAMPLES

EXAMPLE 1

Preparation of the Compound of Formula $(I)_1$

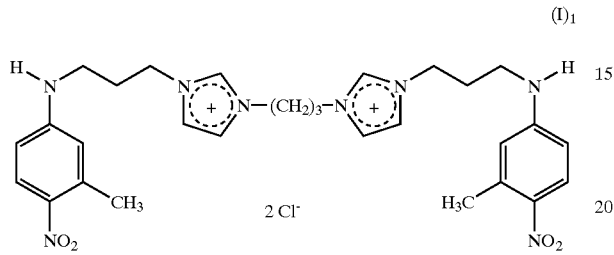

Step 1:

Synthesis of (3-Imidazol-1-ylpropyl)-(3-methyl-4-nitrophenyl)amine

A mixture of 125.2 g (1 mol) of 3-imidazol-1-ylpropylamine (RN 5036–48-6) and 41.4 g (0.3 mol) of potassium carbonate in 140 ml of water was heated to 90° C.

77.6 g (0.5 mol) of 4-fluoro-2-methyl-1-nitrobenzene (RN 446-33-3) were added dropwise over 45 minutes, and the mixture was maintained at 90–95° C. for 2 hours. This mixture was cooled in a bath of ice and the crystalline precipitate was spin-dried, washed with water and dried at 40° C. under vacuum over phosphorous pentoxide.

After recrystallization from refluxing absolute ethanol, 96 g of yellow crystals melting at 133° C. (Kofler) were obtained, the elemental analysis of which, calculated for $C_{13}H_{16}N_4O_2$, was:

| % | C | H | N | O |
|---|---|---|---|---|
| calculated: | 59.99 | 6.20 | 21.52 | 12.29 |
| found: | 59.55 | 6.22 | 21.43 | 12.88 |

Step 2:

Quaternization

A mixture of 88.9 g (0.341 mol) of (3-imidazol-1-ylpropyl)-(3-methyl-4-nitrophenyl)amine obtained in the above step and 19.3 g (0.1705 mol) of 1,3-dichloropropane (RN 142-28-9) in 220 ml of normal pentanol was refluxed for 6 hours. The reaction medium was a solution.

This solution was cooled in a bath of ice: a gum precipitated and was then crystallized in bulk. The product was spin-dried, washed with absolute ethanol, recrystallized from refluxing ethanol and dried at 40° C. under vacuum.

56 g of yellow crystals melting at 138–140° C. (Kofler) were obtained, the elemental analysis of which, calculated for $C_{29}H_{38}N_8O_4Cl_2 \cdot H_2O$, was:

| % | C | H | N | O | Cl |
|---|---|---|---|---|---|
| calculated: | 53.46 | 6.19 | 17.20 | 12.28 | 10.88 |
| found: | 52.69 | 6.25 | 17.06 | 12.89 | 10.99 |

EXAMPLE 2

Preparation of the Compound of Formula $(I)_2$

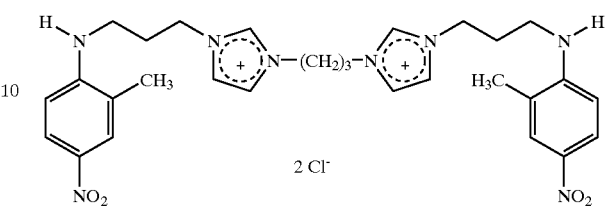

Step 1:

Synthesis of (3-Imidazol-1-ylpropyl)-(2-methyl-4-nitrophenyl)amine

A mixture of 250.4 g (2 mol) of 3-imidazol-1-ylpropylamine (RN 5036-48-6) and 82.8 g (0.6 mol) of potassium carbonate in 280 ml of water was heated to 90° C.

155.1 g (1 mol) of 1-fluoro-2-methyl-4-nitrobenzene (RN 455-88-9) were added dropwise over 30 minutes and this mixture was maintained at 90–95° C. for 4 hours.

The resulting mixture was cooled in a bath of ice and the crystalline product was spin-dried, washed with isopropanol and dried at 40° C. under vacuum.

After recrystallization from refluxing ethanol, 144.8 g of orange-colored crystals melting at 163° C. (Kofler) were obtained, the elemental analysis of which, calculated for $C_{13}H_{16}N_4O_2$, was:

| % | C | H | N | O |
|---|---|---|---|---|
| calculated: | 59.99 | 6.20 | 21.52 | 12.29 |
| found: | 59.60 | 6.15 | 21.46 | 13.12 |

Step 2:

Quaternization

A mixture of 130.1 g (0.5 mol) of (3-imidazol-1-ylpropyl)-(2-methyl-4-nitrophenyl)amine obtained in the above step and 28.25 g (0.25 mol) of 1,3-dichloropropane (RN 142-28-9) in 320 ml of normal pentanol was refluxed for 6 hours.

The reaction medium was a solution.

This solution was cooled in an ice bath and absolute ethanol was added: a gum precipitated and then crystallized.

This product was spin-dried, washed with absolute ethanol and dried at 40° C. under vacuum.

129.6 g of yellow crystals melting at 148–150° C. (Kofler) were obtained, the elemental analysis of which, calculated for $C_{29}H_{38}N_8O_4Cl_2 \cdot 2.5H_2O$, was:

| % | C | H | N | O | Cl |
|---|---|---|---|---|---|
| calculated: | 51.33 | 6.39 | 16.51 | 15.32 | 10.45 |
| found: | 51.69 | 6.45 | 16.62 | 15.38 | 10.33 |

EXAMPLE 3

Preparation of the Compound of Formula (I)$_3$

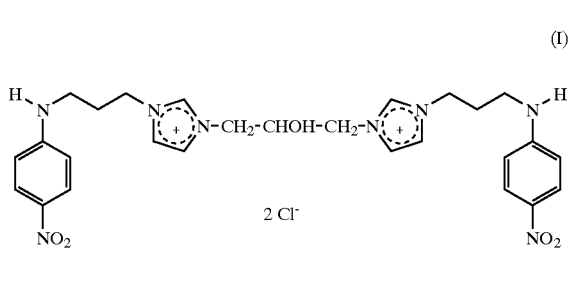

Step 1:

Synthesis of (3-Imidazol-1-ylpropyl)-(4-nitrophenyl)amine

A mixture of 150.2 g (1.2 mol) of 3-imidazol-1-ylpropylamine (RN 5036-48-6) and 139.4 ml (1 mol) of triethylamine in 200 ml of dioxane was heated on a boiling water bath.

141.1 g (1 mol) of 1-fluoro-4-nitrobenzene (RN 350-46-9) were added dropwise over 30 minutes and the mixture was maintained at 90–95° C. for 1 hour.

The resulting mixture was poured into 2 kg of ice-cold water and the crystalline product was spin-dried, washed with water and recrystallized from refluxing ethanol.

106.0 g of yellow crystals melting at 126° C. (Kofler) were obtained, the elemental analysis of which, calculated for $C_{12}H_{14}N_4O_2$, was:

| % | C | H | N | O |
|---|---|---|---|---|
| calculated: | 58.53 | 5.73 | 22.75 | 12.99 |
| found: | 58.33 | 5.83 | 22.81 | 13.41 |

Step 2:

Quaternization

A mixture of 24.6 g (0.1 mol) of (3-imidazol-1-ylpropyl)-(4-nitrophenyl)amine obtained in the above step and 6.45 g (0.05 mol) of 1,3-dichloro-2-propanol (RN 96-23-1) in 100 ml of toluene was refluxed for 8 hours. A gum in suspension crystallized.

The mixture was cooled and the crystalline precipitate was spin-dried, reslurried twice in the minimum amount of absolute ethanol and dried at 45° C. under vacuum.

24.8 g of yellow crystals melting at 228–230° C. (Kofler) were obtained, the elemental analysis of which, calculated for $C_{27}H_{34}N_8O_5Cl_2$, was:

| % | C | H | N | O | Cl |
|---|---|---|---|---|---|
| calculated: | 52.18 | 5.51 | 18.03 | 12.87 | 11.41 |
| found: | 52.23 | 5.55 | 18.03 | 12.80 | 11.44 |

EXAMPLE 4

Preparation of the Compound of Formula (I)$_4$

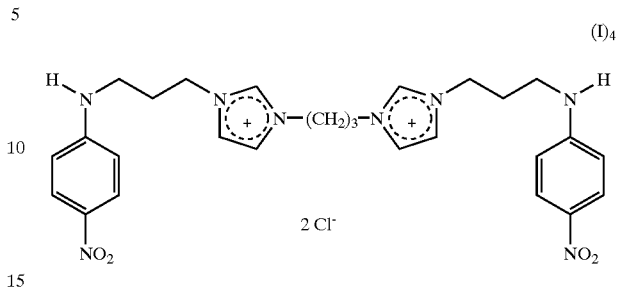

The procedure described for Example 3, step 2, was used.

Starting with 39.4 g (0.16 mol) of (3-imidazol-1-ylpropyl)-(4-nitrophenyl)amine obtained in step 1 of Example 3 and 9.03 g (0.08 mol) of 1,3-dichloropropane (RN 142-28-9), 23.3 g of yellow crystals melting at 186° C. (Kofler) were obtained, the elemental analysis of which, calculated for $C_{27}H_{34}N_8O_4Cl_2 \cdot \frac{1}{3}H_2O$, was:

| % | C | H | N | O | Cl |
|---|---|---|---|---|---|
| calculated: | 53.03 | 5.71 | 18.32 | 11.34 | 11.59 |
| found: | 53.00 | 5.68 | 18.33 | 11.19 | 11.44 |

EXAMPLE 5

Preparation of the Compound of Formula (I)$_5$

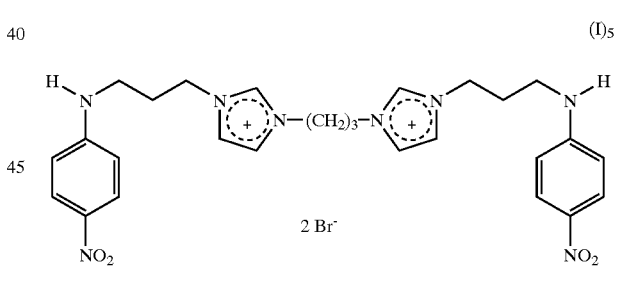

The procedure described for Example 3, step 2, was used.

Starting with 14.8 g (0.06 mol) of (3-imidazol-1-ylpropyl)-(4-nitrophenyl)amine obtained in step 1 of Example 3 and 6.05 g (0.03 mol) of 1,3-dibromopropane (RN 109-64-8), 19.2 g of yellow crystals melting at 203° C. (Kofler) were obtained, the elemental analysis of which, calculated for $C_{27}H_{34}N_8O_4Br_2$, was:

| % | C | H | N | O | Br |
|---|---|---|---|---|---|
| calculated: | 46.70 | 4.94 | 16.14 | 9.22 | 23.01 |
| found: | 46.56 | 5.03 | 16.21 | 9.36 | 22.70 |

EXAMPLE 6

Preparation of the Compound of Formula (I)$_6$

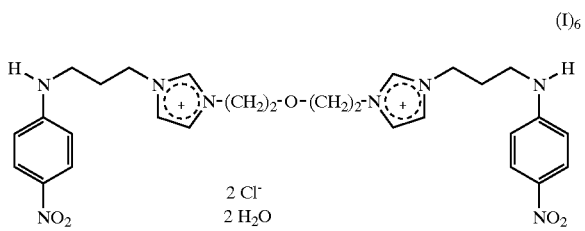

(I)$_6$

The procedure described for Example 3, step 2, was used.

Starting with 24.6 g (0.10 mol) of (3-imidazol-1-ylpropyl)-(4-nitrophenyl)amine obtained in step 1 of Example 3 and 7.15 g (0.05 mol) of 1-chloro-2-(2-chloroethoxy)ethane (RN 111-44-4), 21.6 g of yellow crystals melting at 118–120° C. (Kofler) were obtained, the elemental analysis of which, calculated for $C_{28}H_{36}N_8O_5Cl_2 \cdot 2H_2O$ was:

| % | C | H | N | O | Cl |
|---|---|---|---|---|---|
| calculated: | 50.08 | 6.00 | 16.68 | 16.68 | 10.56 |
| found: | 50.76 | 6.08 | 16.38 | 16.34 | 10.34 |

EXAMPLE 7

Preparation of the Compound of Formula (I)$_7$

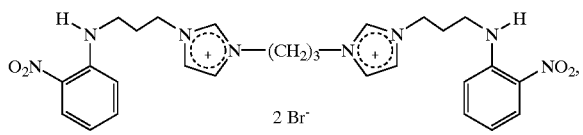

(I)$_7$

Step 1:

Synthesis of (3-Imidazol-1-ylpropyl)-(2-nitrophenyl)amine 187.8 g (1.5 mol) of 3-imidazol-1-ylpropylamine (RN 5036-48-6) and 82.8 g (0.6 mol) of potassium carbonate in 280 ml of water was heated on a boiling water bath.

141.1 g (1 mol) of 1-fluoro-2-nitrobenzene (RN 1493-27-2) were added dropwise over 50 minutes and the mixture was maintained at 90–95° C. for 2 hours.

The resulting mixture was poured into 2 kg of ice-cold water and the crystalline precipitate was spin-dried, washed with water and recrystallized from refluxing isopropyl alcohol.

109.3 g of yellow crystals melting at 80° C. (Kofler) were obtained, the elemental analysis of which, calculated for $C_{12}H_{14}N_4O_2$, was:

| % | C | H | N | O |
|---|---|---|---|---|
| calculated: | 58.53 | 5.73 | 22.75 | 12.99 |
| found: | 58.62 | 5.78 | 22.54 | 13.07 |

Step 2:

Quaternization

The procedure described for Example 3, step 2, was used, with 2-methyl-1-propanol as solvent instead of toluene.

Starting with 74.0 g (0.3 mol) of (3-imidazol-1-ylpropyl)-(2-nitrophenyl)amine obtained in the above step and 30.3 g (0.15 mol) of 1,3-dibromopropane (RN 109-64-8), and after recrystallization from refluxing ethanol, 86.4 g of orange-colored crystals melting at 166° C. (Kofler) were obtained, the elemental analysis of which, calculated for $C_{27}H_{34}N_8O_4Br_2$, was:

| % | C | H | N | O | Br |
|---|---|---|---|---|---|
| calculated: | 46.70 | 4.94 | 16.14 | 9.22 | 23.01 |
| found: | 46.59 | 5.00 | 16.15 | 9.41 | 22.97 |

EXAMPLE 8

Preparation of the Compound of Formula (I)$_8$

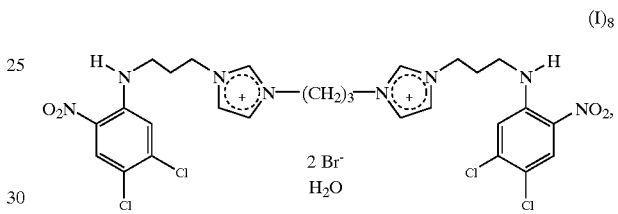

(I)$_8$

Step 1:

Synthesis of (4,5-Dichloro-2-nitro-phenyl)-(3-imidazol-1-ylpropyl)amine

A mixture of 50.1 g (0.45 mol) of 3-imidazol-1-ylpropylamine (RN 5036-48-6) and 62.7 ml (0.45 mol) of triethylamine in 100 ml of 1,2-dimethoxyethane was heated to reflux.

90.6 g (0.4 mol) of 1,2,4-trichloro-5-nitro-benzene (RN 89-69-0) were added portionwise over 30 minutes and the mixture was maintained at reflux for 5 hours.

The resulting mixture was poured into 1.5 kg of ice-cold water and the crystalline precipitate was spin-dried, washed with water and dried at 40° C. under vacuum over phosphorous pentoxide.

After recrystallization from refluxing ethanol, 36 g of orange-yellow crystals melting at 130° C. (Kofler) were obtained, the elemental analysis of which, calculated for $C_{12}H_{12}N_4O_2Cl_2$, was:

| % | C | H | N | O | Cl |
|---|---|---|---|---|---|
| calculated: | 45.73 | 3.84 | 17.78 | 10.15 | 22.50 |
| found: | 45.61 | 3.88 | 17.69 | 10.09 | 22.43 |

Step 2:

Quaternization

The procedure described for Example 3, step 2, was used, with 2-methyl-1-propanol as solvent instead of toluene.

Starting with 47.27 g (0.15 mol) of (4,5-dichloro-2-nitrophenyl)-(3-imidazol-1-ylpropyl)-amine obtained in the above step and 15.15 g (0.075 mol) of 1,3-dibromopropane (RN 109-64-8), and after recrystallization from a refluxing mixture of ethanol and water, 49.0 g of orange-colored crystals melting at about 123–125° C. (Kofler) were obtained, the elemental analysis of which, calculated for $C_{27}H_{30}N_8O_4Cl_4Br_2 \cdot H_2O$, was:

| % | C | H | N | O | Cl | Br |
|---|---|---|---|---|---|---|
| calc.: | 38.14 | 3.79 | 13.18 | 9.41 | 16.68 | 18.8 |
| found: | 37.90 | 3.81 | 13.15 | 9.36 | 16.79 | 19.25 |

EXAMPLE 9

Preparation of the Compound of Formula $(I)_9$

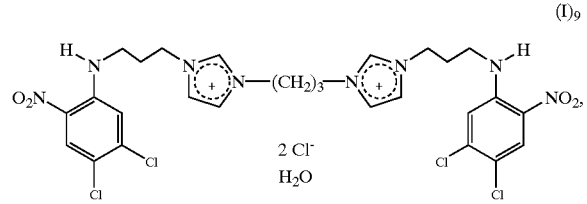

$(I)_9$

Quaternization

Starting with 94.5 g (0.3 mol) of (4,5-dichloro-2-nitrophenyl)-(3-imidazol-1-ylpropyl)-amine obtained in the first step of Example 8 and 16.95 g (0.15 mol) of 1,3-dichloropropane (RN 142-28-9) heated at 150° C. for 19 hours in normal pentanol, and after recrystallization from refluxing ethanol, 38.3 g of orange-colored crystals melting at 224° C. (Kofler) were obtained, the elemental analysis of which, calculated for $C_{27}H_{30}N_8O_4Cl_6 \cdot \frac{1}{2}H_2O$, was:

| % | C | H | N | O | Cl |
|---|---|---|---|---|---|
| calc.: | 43.11 | 4.15 | 14.89 | 9.57 | 28.28 |
| found: | 43.38 | 4.25 | 14.71 | 9.78 | 28.57 |

EXAMPLE 10

Preparation of the Compound of Formula $(I)_{10}$

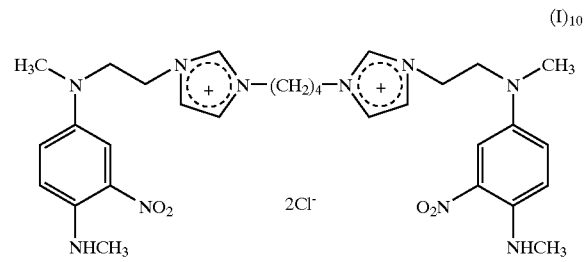

$(I)_{10}$

A mixture of 24.1 g (0.1 mol) of N4-(2-chloroethyl)-N1,N4-dimethyl-2-nitrobenzene-1,4-diamine (RN 14607-54-6) and 10.2 g (0.05 mol) of 1,4-diimidazol-1-ylbutane) (RN 69506-86-1) in 50 ml of isobutanol was heated at the reflux point of the isobutanol for 20 hours.

The crystalline precipitate formed was spin-dried at room temperature.

After purification by recrystallization from refluxing ethanol, 20.3 g of dark violet crystals melting at about 175–177° C. (Kofler) were obtained, the elemental analysis of which, calculated for $C_{30}H_{42}N_{10}O_4Cl_2 \cdot H_2O$, was:

| % | C | M | N | O | Cl |
|---|---|---|---|---|---|
| calc.: | 51.80 | 6.38 | 20.13 | 11.50 | 10.19 |
| found: | 50.79 | 6.43 | 19.39 | 11.50 | 10.20 |

EXAMPLE 11

Preparation of the Compound of Formula $(I)_{11}$

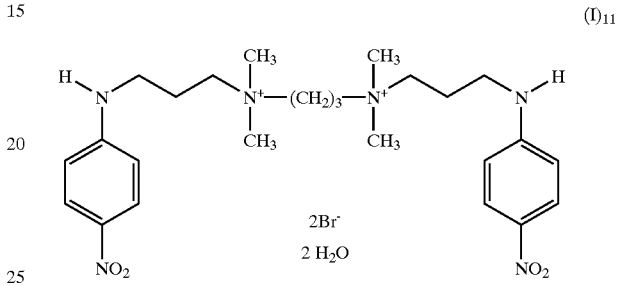

$(I)_{11}$

The procedure described for Example 3, step 2, was used.

Starting with 44.6 g (0.2 mol) of N,N-dimethyl-N'-(4-nitrophenyl)propane-1,3-diamine (RN 25238-54-4) and 20.2 g (0.1 mol) of 1,3-dibromopropane (RN 109-64-8), 47.8 g of yellow crystals melting with decomposition at about 230° C. (Kofler) were obtained, the elemental analysis of which, calculated for $C_{25}H_{40}N_6O_4Br_2 \cdot H_2O$, was:

| % | C | H | N | O | Br |
|---|---|---|---|---|---|
| calc.: | 45.06 | 6.35 | 12.61 | 12.00 | 23.98 |
| found: | 45.15 | 6.35 | 12.36 | 11.61 | 24.02 |

EXAMPLE 12

Preparation of the Compound of Formula $(I)_{12}$

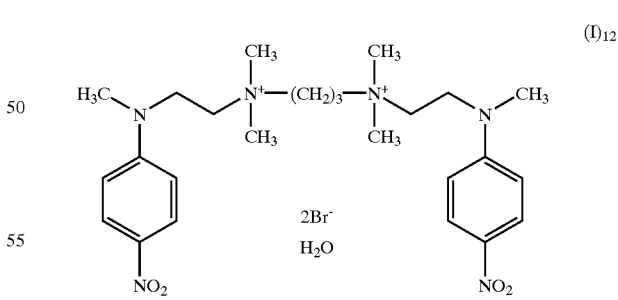

$(I)_{12}$

The procedure described for Example 3, step 2, was used, but with 2-methyl-1-propanol as solvent instead of toluene.

Starting with 53.6 g (0.24 mol) of N,N,N'-trimethyl-N'-(4-nitrophenyl)ethane-1,2-diamine (RN 176665-67-1) and 24.2 g (0.12 mol) of 1,3-dibromopropane (RN 109-64-8), 63.5 g of yellow crystals melting at about 147° C. (Kofler) were obtained, the elemental analysis of which, calculated for $C_{25}H_{40}N_6O_4Br_2 \cdot H_2O$, was:

| % | C | H | N | O | Br |
|---|---|---|---|---|---|
| calc.: | 45.06 | 6.35 | 12.61 | 12.00 | 23.98 |
| found: | 45.04 | 6.38 | 12.60 | 12.68 | 23.98 |

EXAMPLE 13

Preparation of the Compound of Formula $(I)_{13}$

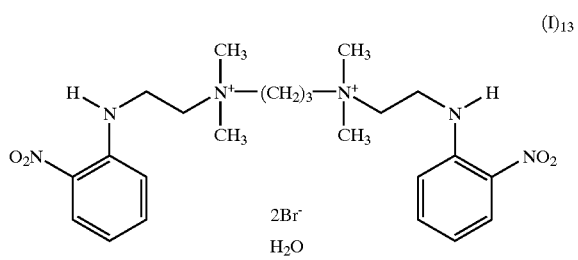

The procedure described for Example 3 was used.

Starting with 62.7 g (0.3 mol) of N,N-dimethyl-N'-(2-nitrophenyl)ethane-1,2-diamine (RN 25238-55-5) and 30.3 9 (0.15 mol) of 1,3-dibromopropane (RN 109-64-8), and after recrystallization from a refluxing mixture of ethanol and water, 67.0 g of yellow crystals melting at 220° C. (Kofler) were obtained, the elemental analysis of which, calculated for $C_{23}H_{36}N_6O_4Br_2 \cdot H_2O$, was:

| % | C | H | N | O | Br |
|---|---|---|---|---|---|
| calc.: | 43.27 | 6.00 | 13.16 | 12.53 | 25.03 |
| found: | 43.24 | 6.14 | 12.59 | 12.72 | 24.74 |

EXAMPLES OF DYE COMPOSITIONS

Examples 1 to 6

The 6 dye compositions collated in the table below were prepared (all contents expressed in grams—A.M. denotes active material):

| | Ex. 1 | Ex. 2 | Ex. 3 | Ex. 4 | Ex. 5 | Ex. 6 |
|---|---|---|---|---|---|---|
| Dye of formula $(I)_3$ | 0.311 | | | | | |
| Dye of formula $(I)_6$ | | 0.318 | | | | |
| Dye of formula $(I)_4$ | | | 0.303 | | | |
| Dye of formula $(I)_{11}$ | | | | 0.333 | | |
| Dye of formula $(I)_7$ | | | | | 0.347 | |
| Dye of formula $(I)_{13}$ | | | | | | 0.319 |
| Hydroxyethyl-cellulose sold under the name NATROSOL 250 MR by the company Aqualon | 0.72 | 0.72 | 0.72 | 0.72 | 0.72 | 0.72 |
| Benzyl alcohol | 4 | 4 | 4 | 4 | 4 | 4 |
| Polyethylene glycol with 6 ethylene oxide | 6 | 6 | 6 | 6 | 6 | 6 |
| (C8—C10)alkyl | 4.5 | 4.5 | 4.5 | 4.5 | 4.5 | 4.5 |

-continued

| | Ex. 1 | Ex. 2 | Ex. 3 | Ex. 4 | Ex. 5 | Ex. 6 |
|---|---|---|---|---|---|---|
| polyglucoside as an aqueous solution con-taining 60% A.M., sold under the name ORAMIX CG 110 by the company SEPPIC | A.M. | A.M. | A.M. | A.M. | A.M. | A.M. |
| Phosphate buffer pH 7 qs | 100 | 100 | | 100 | 100 | |
| Phosphate buffer pH 9 (boric acid/potassium chloride/sodium hydroxide qs | | | 100 | | | 100 |

Example 7

The direct dye composition below was prepared: (all contents expressed in grams—A.M. denotes active material)

| | Example 7 |
|---|---|
| Dye of formula $(I)_{23}$ | 0.696 |
| Hydroxyethylcellulose sold under the name NATROSOL 250 MR by the company Aqualon | 0.384 |
| Benzyl alcohol | 4 |
| Polyethylene glycol-400 | 6 |
| (C8—C10)Alkyl polyglucoside as an aqueous solution containing 60% A.M., sold under the name ORAMIX CG 110 by the company SEPPIC | 5 A.M. |
| pH 9 phosphate buffer (boric acid/potassium chloride/sodium hydroxide qs | 100 |

Each of the above compositions was applied to locks of natural or permanent-waved grey hair containing 90% white hairs, and was left to stand on the hair for 20 minutes. After rinsing with running water and drying, the hair was dyed in a shade given in the table below.

| Composition of Example 1 | intense matte yellow |
|---|---|
| Composition of Example 2 | intense matte yellow |
| Composition of Example 3 | intense matte yellow |
| Composition of Example 4 | intense matte yellow |
| Composition of Example 5 | intense orange yellow |
| Composition of Example 6 | intense yellow |
| Composition of Example 7 | violet |

What is claimed is:

1. A dye composition for keratin substances, comprising, in a medium which is suitable for dyeing, at least one compound of formula (I) below or an acid addition salt thereof, said at least one compound of formula (I) being present in said composition in an amount effective for direct dyeing of keratinous substances:

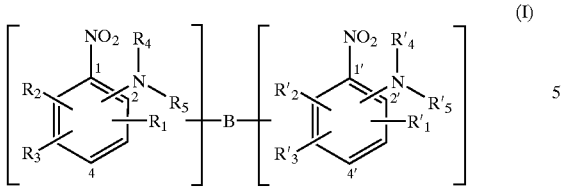

wherein:

B is a linker arm which is a linear or branched alkyl chain, which can be interrupted with one or more groups Z as defined below and/or with one or more hetero atoms, can be optionally substituted with one or more hydroxyl or $C_1$–$C_6$ alkoxy radicals, and can bear one or more ketone functions;

$R_1$, $R_2$, $R_3$, $R'_1$, $R'_2$ and $R'_3$, which may be identical or different, are chosen from one of the two valencies of a linker arm B; a hydrogen atom; a halogen atom; a group Z as defined below; a ($C_1$–$C_6$)alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$) alkyl radical; an N—($C_1$–$C_6$)alkylamino($C_1$–$C_6$) alkylcarbonyl($C_1$–$C_6$)alkyl radical; an N,N-di($C_1$–$C_6$) alkylamino($C_1$–$C_6$)alkylcarbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical, an N—Z-aminosulphonyl radical; an N—($C_1$–$C_6$)alkylaminosulphonyl radical; an N,N-di ($C_1$–$C_6$)alkylaminosulphonyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; a $C_1$–$C_6$ trifluoroalkyl radical; a cyano radical; an unsubstituted or substituted amino radical, wherein the substituents on the amine, which may be identical or different, have the same definition as the variables $R_4$, $R_5$, $R'_4$ and $R'_5$ as defined below; an amino($C_1$–$C_6$)alkyl radical wherein the alkyl is unsubstituted or substituted with one or more hydroxyl radicals and wherein the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$)alkylcarbamyl or N,N-di($C_1$–$C_6$) alkylcarbamyl, $C_1$–$C_6$ alkylsulphonyl, formyl, trifluoro ($C_1$–$C_6$)alkylcarbonyl, ($C_1$–$C_6$)alkylcarboxyl and thiocarbamyl radicals, or a group Z as defined below; and a group —$OR_6$ or —$SR_6$, wherein $R_6$ is as defined below;

$R_6$ is chosen from one of the two valencies of a linker arm B; a hydrogen atom; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy ($C_1$–$C_6$)alkyl radical; an aryl radical; a benzyl radical; a carboxy($C_1$–$C_6$)alkyl radical; a (($C_1$–$C_6$)alkylcarboxy ($C_1$–$C_6$)alkyl radical; a cyano($C_1$–$C_6$)alkyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$) alkylcarbonyl($C_1$–$C_6$)alkyl radical; and a $C_1$–$C_6$ aminoalkyl radical; a $C_1$–$C_6$ aminoalkyl radical wherein the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro($C_1$–$C_6$)alkylcarbonyl, ($C_1$–$C_6$)alkylcarboxyl, carbamyl, N—($C_1$–$C_6$) alkylcarbamyl, N,N-di-($C_1$–$C_6$)alkylcarbamyl, thiocarbamyl and $C_1$–$C_6$ alkylsulphonyl radicals, or a group Z as defined below;

$R_4$, $R_5$, $R'_4$ and $R'_5$, which may be identical or different, are chosen from one of the two valencies of a linker arm B; a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; an aryl radical; a benzyl radical; a cyano($C_1$–$C_6$)alkyl radical; a carbamyl ($C_1$–$C_6$)alkyl radical; an N—($C_1$–$C_6$)alkylcarbamyl ($C_1$–$C_6$)alkyl radical; an N,N-di($C_1$–$C_6$)alkylcarbamyl ($C_1$–$C_6$)alkyl radical; a thiocarbamyl($C_1$–$C_6$)alkyl radical; a $C_1$–$C_6$ trifluoroalkyl radical; a $C_1$–$C_6$ sulphoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; and a $C_1$–$C_6$ aminoalkyl radical; a $C_1$–$C_6$ aminoalkyl radical wherein the alkyl is unsubstituted or substituted with one or more hydroxyl radicals and wherein the amine is substituted with one or two identical or different radicals chosen from alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$)alkylcarbamyl or N,N-di ($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or a group Z as defined below;

Z is chosen from the unsaturated cationic groups of formulae (II) and (III) below, and the saturated cationic groups of formula (IV) below:

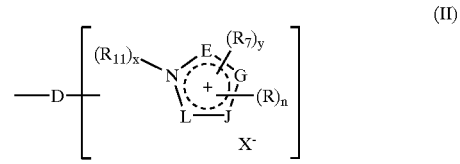

-continued

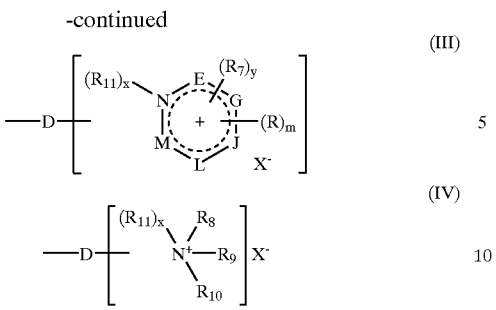

wherein:
D is a linker arm which is a linear or branched alkyl chain, which can be interrupted by one or more hetero atoms, can be substituted with one or more hydroxyl or $C_1$–$C_6$ alkoxy radicals, and can bear one or more ketone functions;

the ring members E, G, J, L and M, which may be identical or different, are chosen from carbon, oxygen, sulphur and nitrogen atoms;

n is an integer ranging from 0 to 4;

m is an integer ranging from 0 to 5;

the radicals R, which may be identical or different, are chosen from one of the two valencies of a linker arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical, a nitro radical; a cyano radical; a cyano($C_1$–$C_6$)alkyl radical; a $C_1$–$C_6$ alkoxy radical; a tri($C_1$–$C_6$)alkylsilane($C_1$–$C_6$)alkyl radical; an amido radical; an aldehydo radical; a carboxyl radical; a ($C_1$–$C_6$)alkylcarbonyl radical; a thio radical; a $C_1$–$C_6$ thioalkyl radical; a $C_1$–$C_6$ alkylthio radical; an amino radical; an amino radical protected with a ($C_1$–$C_6$)alkylcarbonyl, carbamyl or $C_1$–$C_6$ alkylsulphonyl radical; and a group NHR" or NR"R wherein R" and R, which may be identical or different, are chosen from a $C_1$–$C_6$ alkyl radical, a $C_1$–$C_6$ monohydroxyalkyl radical and a $C_2$–$C_6$ polyhydroxyalkyl radical;

$R_7$ is chosen from one of the two valencies of a linker arm B; a $C_1$–$C_6$ alkyl radical; a $C_1$–$C_6$ monohydroxyalkyl radical; a $C_2$–$C_6$ polyhydroxyalkyl radical; a cyano($C_1$–$C_6$)alkyl radical; a tri($C_1$–$C_6$)alkylsilane($C_1$–$C_6$)alkyl radical; a ($C_1$–$C_6$)alkoxy($C_1$–$C_6$)alkyl radical; a carbamyl-($C_1$–$C_6$)alkyl radical; a ($C_1$–$C_6$)alkylcarboxy($C_1$–$C_6$)-alkyl radical; a benzyl radical; and a second group Z which is identical to or different from the first group Z;

$R_8$, $R_9$ and $R_{10}$, which may be identical or different, are chosen from one of the two valencies of a linker arm B; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a cyano($C_1$–$C_6$)alkyl radical; an aryl radical; a benzyl radical; a $C_1$–$C_6$ amidoalkyl radical; a tri($C_1$–$C_6$)alkylsilane($C_1$–$C_6$)alkyl radical; and a $C_1$–$C_6$ aminoalkyl radical wherein the amine is protected with a ($C_1$–$C_6$) alkylcarbonyl, carbamyl or $C_1$–$C_6$ alkylsulphonyl radical; or wherein two of the radicals $R_8$, $R_9$ and $R_{10}$ together form, with the nitrogen atom to which they are attached, a saturated 5- or 6-membered carbon-based ring which can contain one or more hetero atoms, wherein said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$) alkyl radical, a thio radical, a $C_1$–$C_6$ thioalkyl radical, a $C_1$–$C_6$ alkylthio radical, an amino radical, or an amino radical protected with a ($C_1$–$C_6$) alkylcarbonyl, carbamyl or $C_1$–$C_6$ alkylsulphonyl radical; or further wherein one of the radicals $R_8$, $R_9$ and $R_{10}$ is a second group Z which is identical to or different from the first group Z;

$R_{11}$ is chosen from one of the two valencies of a linker arm B; a $C_1$–$C_6$ alkyl radical; a $C_1$–$C_6$ monohydroxy-alkyl radical; a $C_2$–$C_6$ polyhydroxy-alkyl radical; an aryl radical; a benzyl radical; a $C_1$–$C_6$ aminoalkyl radical; a $C_1$–$C_6$ aminoalkyl radical wherein the amine is protected with a ($C_1$–$C_6$) alkylcarbonyl, carbamyl or $C_1$–$C_6$ alkylsulphonyl radical; a carboxy($C_1$–$C_6$)alkyl radical; a cyano ($C_1$–$C_6$)alkyl radical; a carbamyl($C_1$–$C_6$)alkyl radical; a $C_1$–$C_6$ trifluoroalkyl radical; a tri($C_1$–$C_6$) alkylsilane-($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphinyl ($C_1$–$C_6$)alkyl radical; a ($C_1$–$C_6$)alkylsulphonyl ($C_1$–$C_6$)alkyl radical; a ($C_1$–$C_6$)alkylketo($C_1$–$C_6$) alkyl radical; an N—($C_1$–$C_6$)alkylcarbamyl($C_1$–$C_6$) alkyl radical; and an N—($C_1$–$C_6$)alkylsulphonamido ($C_1$–$C_6$)alkyl radical;

x and y are integers equal to 0 or 1; with the provisos that:

in the unsaturated cationic groups of formula (II):
when x=0, the linker arm D is attached to the nitrogen atom,
when x=1, the linker arm D is attached to one of the ring members E, G, J or L,
y can take the value 1 only when:
1) the ring members E, G, J and L are all carbon atoms and when the radical $R_7$ is borne by the nitrogen atom of the unsaturated ring; or
2) at least one of the ring members E, G, J and L is a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is a divalent atom and when the radical $R_7$ is borne by the nitrogen atom of the unsaturated ring;

in the cationic groups of formula (IV):
when x=0, the linker arm D is attached to the nitrogen atom bearing the radicals $R_8$, $R_9$ and $R_{10}$,
when x=1, two of the radicals $R_8$, $R_9$ and $R_{10}$ form, together with the nitrogen atom to which they are attached, a saturated 5- or 6-membered carbon-based ring which can contain one or more hetero atoms, wherein said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical, or an amino radical protected with a ($C_1$–$C_6$)alkylcarbonyl, carbamyl or $C_1$–$C_6$ alkylsulphonyl radical; and the linker arm D is borne by a carbon atom of said saturated ring;

$X^-$ is a monovalent or divalent anion;

with the proviso that said at least one compound of formula (I) comprises at least one cationic group Z, wherein at least one of the following applies:

a) said linker arm B is interrupted with one or more groups Z, b) at least one of said $R_1$, $R_2$, $R_3$, $R_4$, $R_5$, $R'_1$, $R'_2$, $R'3$, $R'_4$ and $R'_5$ comprises at least one Z group.

2. A composition according to claim 1, wherein said keratin substances are human keratin fibers.

3. A composition according to claim 2, wherein said human keratin fibers are hair.

4. A composition according to claim 1, wherein B is a linear or branched alkyl chain comprising from 1 to 14 carbon atoms.

5. A composition according to claim 1, wherein B is a linear or branched alkyl chain, which is interrupted by one or more hetero atoms chosen from oxygen, sulphur and nitrogen atoms.

6. A composition according to claim 1, wherein D is a linear or branched alkyl chain comprising from 1 to 14 carbon atoms.

7. A composition according to claim 1, wherein D is a linear or branched alkyl chain, which is interrupted by one or more hetero atoms chosen from oxygen, sulphur and nitrogen atoms.

8. A composition according to claim 1, wherein the rings of the unsaturated groups Z of formula (II) are chosen from pyrrole, imidazole, pyrazole, oxazole, thiazole and triazole rings.

9. A composition according to claim 1, wherein the rings of the unsaturated groups Z of formula (III) are chosen from pyridine, pyrimidine, pyrazine, oxazine and triazine rings.

10. A composition according to claim 1, wherein two of the radicals $R_8$, $R_9$ and $R_{10}$ in formula (IV) together form, with the nitrogen atom to which they are attached, a pyrrolidine ring, a piperidine ring, a piperazine ring or a morpholine ring, wherein said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$) alkylcarbonyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical.

11. A composition according to claim 1, wherein $X^-$ is chosen from a halogen atom, a hydroxide, a hydrogen sulphate and a ($C_1$–$C_6$)alkyl sulphate.

12. A composition according to claim 1, wherein said at least one compound of formula (I) is chosen from those of formulae $(I)_1$ to $(I)_{23}$ below:

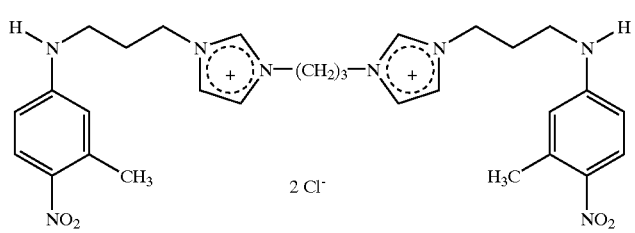

$(I)_1$

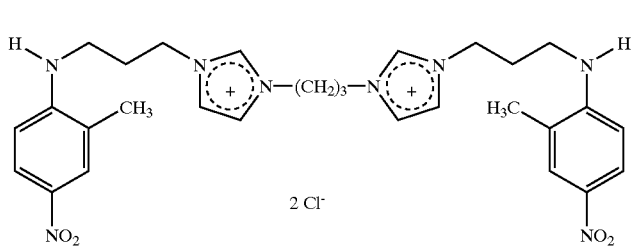

$(I)_2$

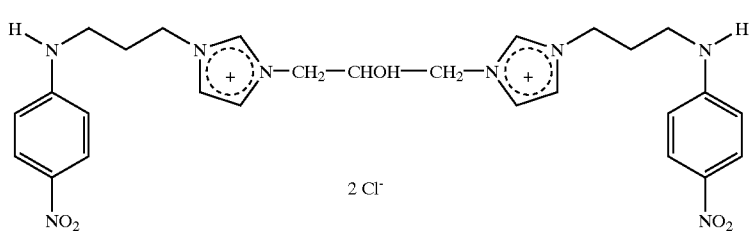

$(I)_3$

-continued
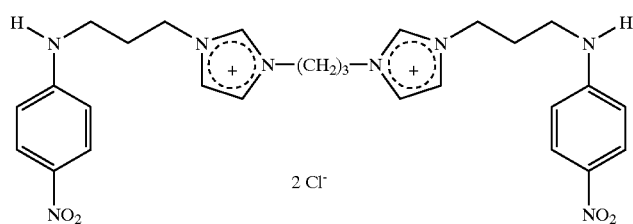
(I)4
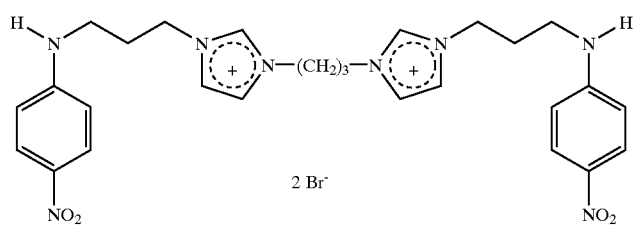
(I)5
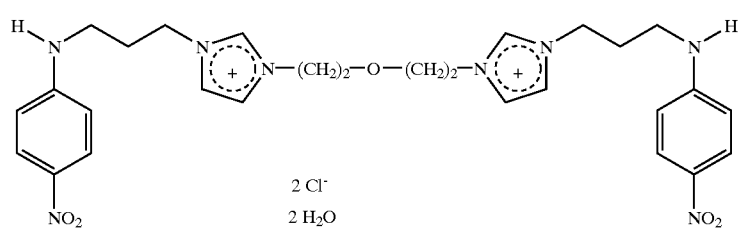
(I)6
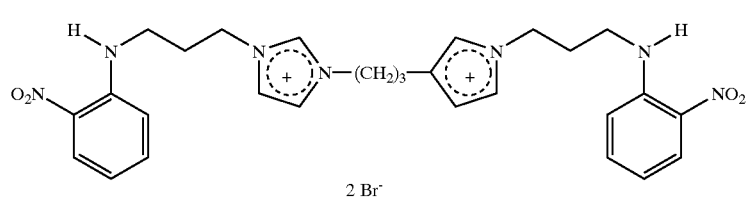
(I)7
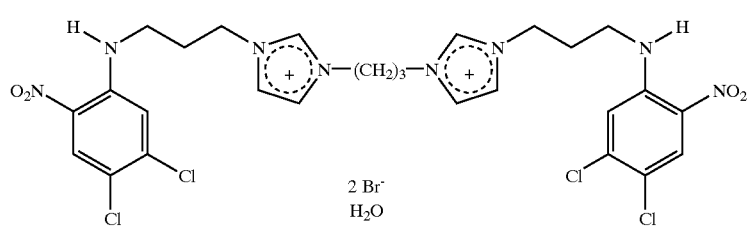
(I)8
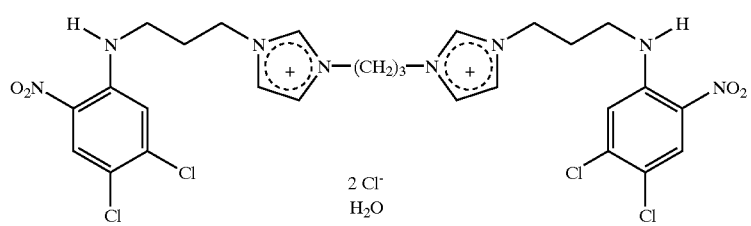
(I)9
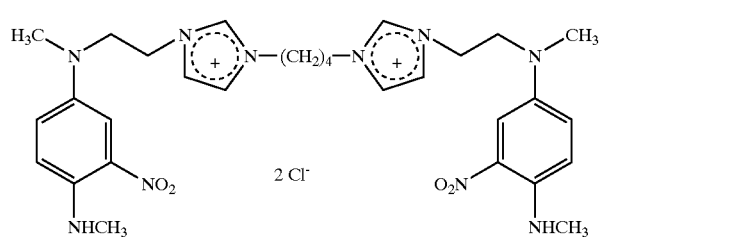
(I)10

-continued
(I)₁₁
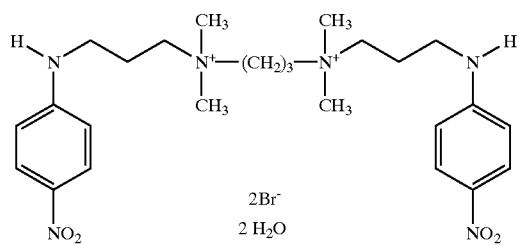
(I)₁₂
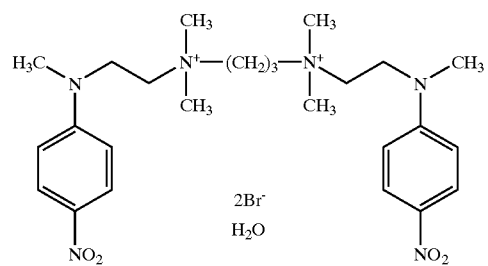
(I)₁₃
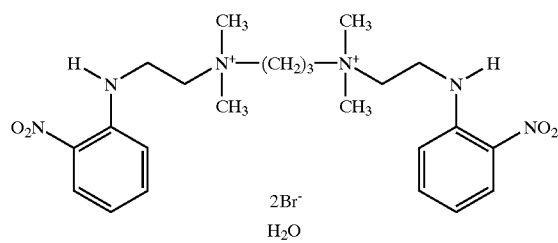
(I)₁₄
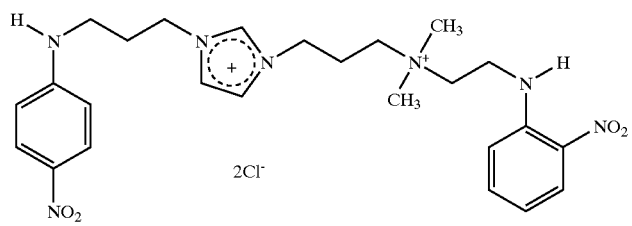
(I)₁₅
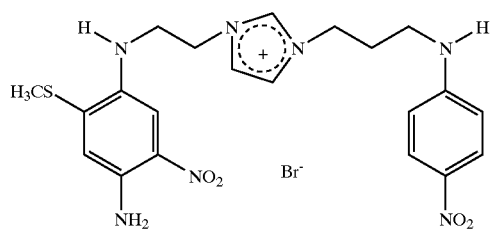
(I)₁₆
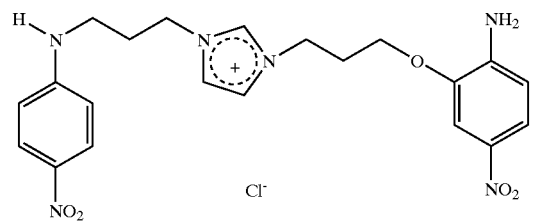
(I)₁₇
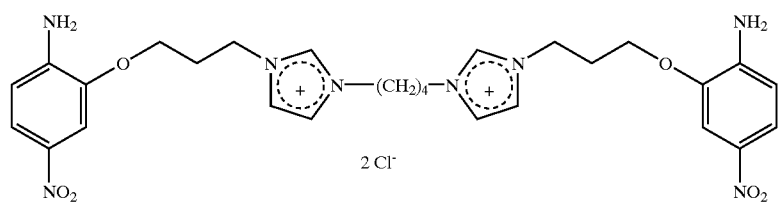
(I)₁₈
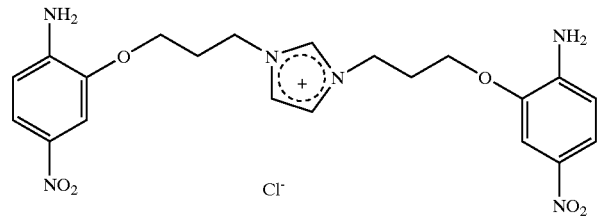
(I)₁₉
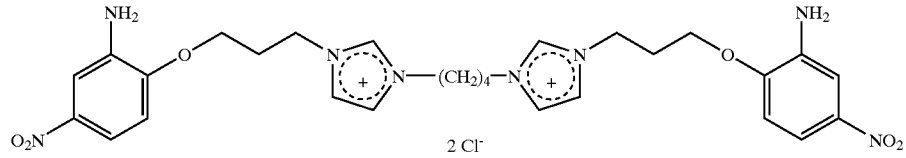

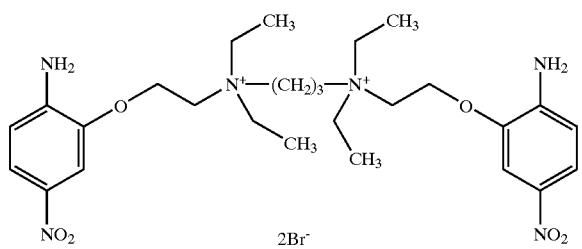 (I)₂₀

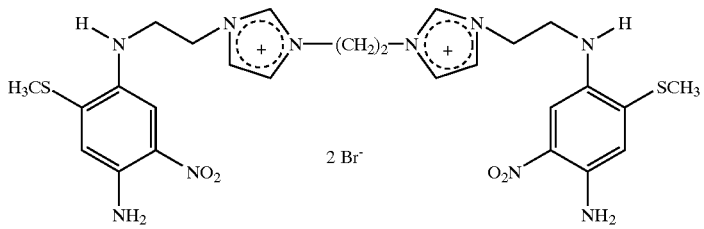 (I)₂₁

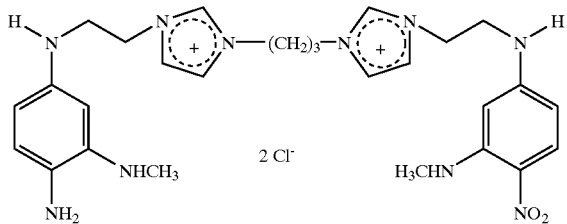 (I)₂₂

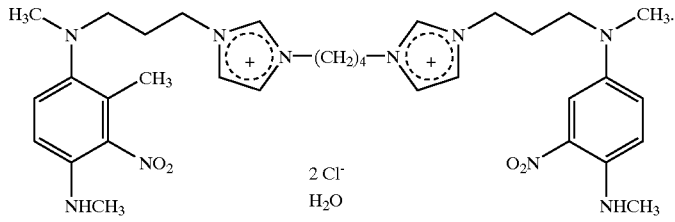 (I)₂₃

13. A composition according to claim 1, wherein said acid addition salts are chosen from hydrochlorides, hydrobromides, sulphates, citrates, succinates, tartrates, lactates and acetates.

14. A composition according to claim 1 wherein said composition has a pH ranging from 3 to 12.

15. A composition according to claim 1, wherein said at least one compound of formula (I) is present in an amount ranging from 0.005 to 12% by weight relative to the total weight of the composition.

16. A composition according to claim 15, wherein said at least one compound of formula (I) is present in an amount ranging from 0.05 to 6% by weight relative to the total weight of the composition.

17. A composition according to claim 1, wherein said medium which is suitable for dyeing is an aqueous medium comprising water and/or organic solvents, said medium being present in said composition in an amount ranging from 1 to 40% by weight relative to the total weight of the composition.

18. A process for dyeing keratin fibers by direct dyeing, comprising applying a dyeing composition to wet or dry keratin fibers, said dyeing composition comprising, in a medium appropriate for dyeing, at least one compound of formula (I) below or an acid addition salt thereof, said at least one compound of formula (I) being present in said composition in an amount effective for direct dyeing of keratin fibers:

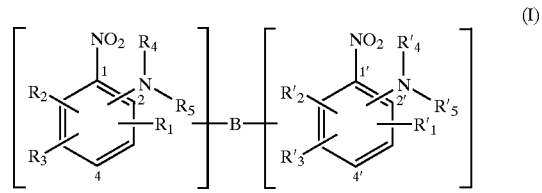 (I)

wherein:
B is a linker arm which is a linear or branched alkyl chain, which can be interrupted with one or more groups Z as defined below and/or with one or more hetero atoms, can be optionally substituted with one or more hydroxyl or $C_1$–$C_6$ alkoxy radicals, and can bear one or more ketone functions;

$R_1$, $R_2$, $R_3$, $R'_1$, $R'_2$ and $R'_3$, which may be identical or different, are chosen from one of the two valencies of a linker arm B; a hydrogen atom; a halogen atom; a group Z as defined below; a ($C_1$–$C_6$)alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$) alkyl radical; an N—($C_1$–$C_6$)alkylamino($C_1$–$C_6$) alkylcarbonyl($C_1$–$C_6$)alkyl radical; an N,N-di($C_1$–$C_6$) alkylamino($C_1$–$C_6$)alkylcarbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N—Z-aminosulphonyl radical; an N—($C_1$–$C_6$) alkylaminosulphonyl radical; an N,N-di($C_1$–$C_6$) alkylaminosulphonyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_5$)alkoxy($C_1$–$C_6$) alkyl radical; a $C_1$–$C_6$ trifluoroalkyl radical; a cyano radical; an unsubstituted or substituted amino radical, wherein the substituents on the amine, which may be identical or different, have the same definition as the variables $R_4$, $R_5$, $R'_4$ and $R'_5$ as defined below; an amino($C_1$–$C_6$)alkyl radical wherein the alkyl is unsubstituted or substituted with one or more hydroxyl radicals and wherein the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$)alkylcarbamyl or N,N-di($C_1$–$C_6$) alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or a group Z as defined below; and a group —$OR_6$ or —$SR_6$, wherein $R_6$ is as defined below;

$R_6$ is chosen from one of the two valencies of a linker arm B; a hydrogen atom; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy ($C_1$–$C_6$)alkyl radical; an aryl radical; a benzyl radical; a carboxy($C_1$–$C_6$)alkyl radical; a ($C_1$–$C_6$)alkylcarboxy ($C_1$–$C_6$)alkyl radical; a cyano($C_1$–$C_6$)alkyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$ trifluoroalkyl radical; a $C_1$–$C_6$ aminosulphonylalkyl radical, a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$) alkylcarbonyl($C_1$–$C_6$)alkyl radical; and a $C_1$–$C_6$ aminoalkyl radical: a $C_1$–$C_6$ aminoalkyl radical wherein the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro($C_1$–$C_6$)alkylcarbonyl, ($C_1$–$C_6$)alkylcarboxyl, carbamyl, N—($C_1$–$C_6$) alkylcarbamyl, N,N-di-($C_1$–$C_6$)alkylcarbamyl, thiocarbamyl and $C_1$–$C_6$ alkylsulphonyl radicals, or a group Z as defined below;

$R_4$, $R_5$, $R'_4$ and $R'_5$, which may be identical or different, are chosen from one of the two valencies of a linker arm B; a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; an aryl radical; a benzyl radical; a cyano($C_1$–$C_6$)alkyl radical; a carbamyl ($C_1$–$C_6$)alkyl radical; an N—($C_1$–$C_6$)alkylcarbamyl ($C_1$–$C_8$)alkyl radical; an N,N-di($C_1$–$C_6$)alkylcarbamyl ($C_1$–$C_6$)alkyl radical; a thiocarbamyl($C_1$–$C_6$)alkyl radical; a $C_1$–$C_6$ trifluoroalkyl radical; a $C_1$–$C_6$ sulphoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; and a $C_1$–$C_6$ aminoalkyl radical; a $C_1$–$C_6$ aminoalkyl radical wherein the alkyl is unsubstituted or substituted with one or more hydroxyl radicals and wherein the amine is substituted with one or two identical or different radicals chosen from alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$)alkylcarbamyl or N,N-di ($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or a group Z as defined below;

Z is chosen from the unsaturated cationic groups of formulae (II) and (III) below, and the saturated cationic groups of formula (IV) below:

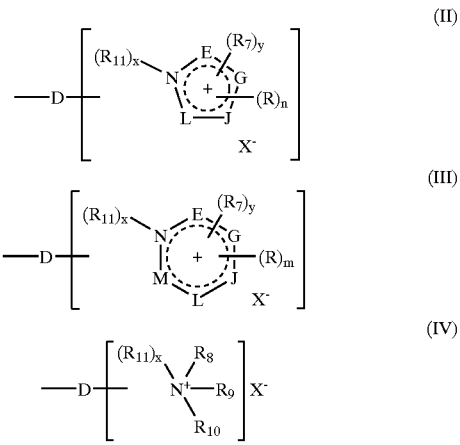

wherein:

D is a linker arm which is a linear or branched alkyl chain, which can be interrupted by one or more hetero atoms, can be substituted with one or more hydroxyl or $C_1$–$C_6$ alkoxy radicals, and can bear one or more ketone functions;

the ring members E, G, J, L and M, which may be identical or different, are chosen from carbon, oxygen, sulphur and nitrogen atoms;

n is an integer ranging from 0 to 4;

m is an integer ranging from 0 to 5;

the radicals R, which may be identical or different, are chosen from one of the two valencies of a linker arm B; a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a cyano($C_1$–$C_6$)alkyl radical; a $C_1$–$C_6$ alkoxy radical; a tri($C_1$–$C_6$)alkylsilane($C_1$–$C_6$)alkyl radical; an amido radical; an aldehydo radical; a carboxyl radical; a ($C_1$–$C_6$)alkylcarbonyl radical; a thio radical; a $C_1$–$C_6$ thioalkyl radical; a $C_1$–$C_6$ alkylthio radical; an amino radical; an amino radical protected with a ($C_1$–$C_6$)alkylcarbonyl, carbamyl or $C_1$–$C_6$ alkylsulphonyl radical; and a group NHR" or NR"R wherein R" and R, which may be identical or different, are chosen from a $C_1$–$C_6$ alkyl radical, a $C_1$–$C_6$ monohydroxyalkyl radical and a $C_2$–$C_6$ polyhydroxyalkyl radical;

$R_7$ is chosen from one of the two valencies of a linker arm B; a $C_1$–$C_6$ alkyl radical; a $C_1$–$C_6$ monohydroxyalkyl radical; a $C_2$–$C_6$ polyhydroxyalkyl radical, a cyano($C_1$–$C_6$)alkyl radical; a tri($C_1$–$C_6$)alkylsilane($C_1$–$C_6$)alkyl radical; a ($C_1$–$C_6$)alkoxy($C_1$–$C_6$)alkyl radical; a carbamyl-($C_1$–$C_6$)alkyl radical; a ($C_1$–$C_6$)alkylcarboxy($C_1$–$C_6$)-alkyl radical; a benzyl radical; and a second group Z which is identical to or different from the first group Z;

$R_8$, $R_9$ and $R_{10}$, which may be identical or different, are chosen from one of the two valencies of a linker arm B; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a cyano($C_1$–$C_6$)alkyl radical; an aryl radical; a benzyl radical; a $C_1$–$C_6$ amidoalkyl radical; a tri($C_1$–$C_6$)alkylsilane($C_1$–$C_6$)alkyl radical; and a $C_1$–$C_6$ aminoalkyl radical wherein the amine is protected with a ($C_1$–$C_6$)alkylcarbonyl, carbamyl or $C_1$–$C_6$ alkylsulphonyl radical; or wherein two of the radicals $R_8$, $R_9$ and $R_{10}$ together form, with the nitrogen atom to which they are attached, a saturated 5- or 6-membered carbon-based ring which can contain one or more hetero atoms, wherein said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical, or an amino radical protected with a ($C_1$–$C_6$)alkylcarbonyl, carbamyl or $C_1$–$C_6$ alkylsulphonyl radical; or further wherein one of the radicals $R_8$, $R_9$ and $R_{10}$ is a second group Z which is identical to or different from the first group Z;

$R_{11}$ is chosen from one of the two valencies of a linker arm B; a $C_1$–$C_6$ alkyl radical; a $C_1$–$C_6$ monohydroxy-alkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical wherein the amine is protected with a ($C_1$–$C_6$)alkylcarbonyl, carbamyl or $C_1$–$C_6$ alkylsulphonyl radical; a carboxy($C_1$–$C_6$)alkyl radical; a cyano($C_1$–$C_6$)alkyl radical; a carbamyl($C_1$–$C_6$)alkyl radical; a $C_1$–$C_6$ trfluoroalkyl radical; a tri($C_1$–$C_6$)alkylysilane-($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; and an N—($C_1$–$C_6$)alkylsulphonamido($C_1$–$C_6$)alkyl radical;

x and y are integers equal to 0 or 1; with the provisos that:

in the unsaturated cationic groups of formula (II):
when x=0, the linker arm D is attached to the nitrogen atom,
when x=1, the linker arm D is attached to one of the ring members E, G, J or L,
y can take the value 1 only when:
1) the ring members E, G, J and L are all carbon atoms and when the radical $R_7$ is borne by the nitrogen atom of the unsaturated ring; or
2) at least one of the ring members E, G, J and L is a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is a divalent atom and when the radical $R_7$ is borne by the nitrogen atom of the unsaturated ring;

in the cationic groups of formula (IV):
when x=0, the linker arm D is attached to the nitrogen atom bearing the radicals $R_8$, $R_9$ and $R_{10}$,
when x=1, two of the radicals $R_8$, $R_9$ and $R_{10}$ form, together with the nitrogen atom to which they are attached, a saturated 5- or 6-membered carbon-based ring which can contain one or more hetero atoms, wherein said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical, or an amino radical protected with a ($C_1$–$C_6$)alkylcarbonyl, carbamyl or $C_1$–$C_6$ alkylsulphonyl radical; and the linker arm D is borne by a carbon atom of said saturated ring;

$X^-$ is a monovalent or divalent anion;
with the proviso that said at least one compound of formula (I) comprises at least one cationic group Z, wherein at least one of the following applies:
a) said linker arm B is interrupted with one or more groups Z,
b) at least one of said $R_1$, $R_2$, $R_3$, $R_4$, $R_5$, $R'_1$, $R'_2$, $R'_3$, $R'_4$ and $R'_5$ comprises at least one Z group.

19. A process according to claim 18, wherein said keratin fibers are human keratin fibers.

20. A process according to claim 19, wherein said human keratin fibers are hair.

21. A process according to claim 18, wherein said dyeing composition is applied to wet or dry keratin fibers, and said fibers are dried without intermediate rinsing.

22. A process according to claim 18, wherein said dyeing composition is applied to wet or dry keratin fibers, and, after optionally leaving said composition to act on said fibers for an exposure time ranging from 3 to 60 minutes, said fibers are rinsed, optionally washed, rinsed again and dried.

* * * * *

UNITED STATES PATENT AND TRADEMARK OFFICE
CERTIFICATE OF CORRECTION

PATENT NO. : 6,468,316 B1
DATED : October 22, 2002
INVENTOR(S) : Alain Genet et al.

It is certified that error appears in the above-identified patent and that said Letters Patent is hereby corrected as shown below:

Column 25,
Line 33, "radical," should read -- radical; --.

Column 27,
Line 31, "radical," should read -- radical; --.

Column 29,
Line 15, "R'3" should read -- $R'_3$ --.

Column 31,
Structure $(I)_7$,

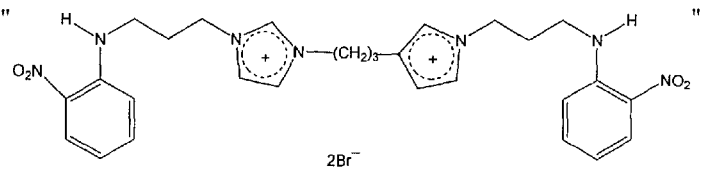

should read

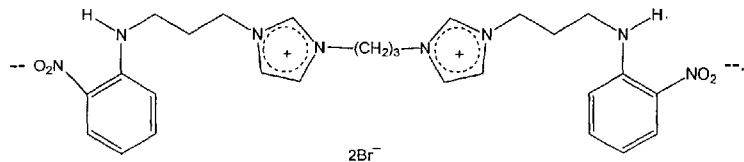

Column 35,
Structure $(I)_{22}$,

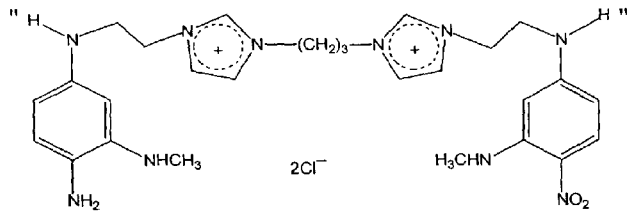

should read

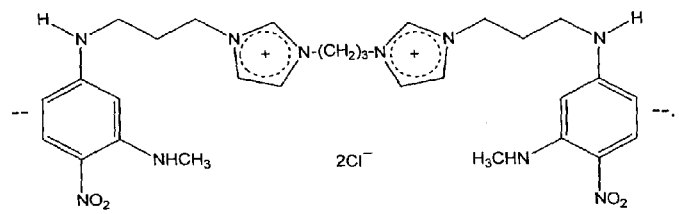

UNITED STATES PATENT AND TRADEMARK OFFICE
CERTIFICATE OF CORRECTION

PATENT NO. : 6,468,316 B1
DATED : October 22, 2002
INVENTOR(S) : Alain Genet et al.

It is certified that error appears in the above-identified patent and that said Letters Patent is hereby corrected as shown below:

Column 35,
Structure $(I)_{23}$,

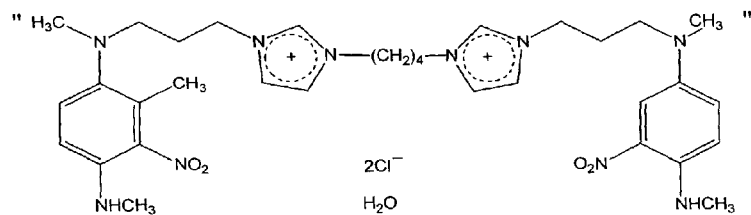

should read

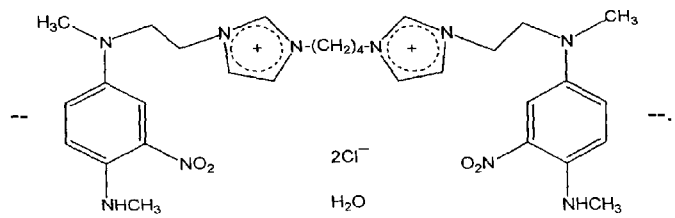

Column 37,
Line 24, "$(C_1-C_5)$" should read -- $(C_1-C_6)$ --.
Line 52, "radical," should read -- radical; --.
Line 59, "radical:" should read -- radical; --.

Column 38,
Line 9, "$(C_1-C_8)$" should read -- $(C_1-C_6)$ --.

Column 39,
Line 17, "radical," should read -- radical; --.

Signed and Sealed this

Eighth Day of April, 2003

JAMES E. ROGAN
*Director of the United States Patent and Trademark Office*